United States Patent [19]
Swayze et al.

[11] Patent Number: 6,058,321
[45] Date of Patent: May 2, 2000

[54] INSTRUMENT FOR CONTINUOUSLY MONITORING FETAL HEART RATE AND INTERMITTENTLY MONITORING FETAL BLOOD PH AND METHOD OF USE

[76] Inventors: Claude R. Swayze, 27 Benhill Rd., St. Paul, Minn. 55105; James W. Halvorson, 2716 Yukon Ave. N., New Hope, Minn. 55427; Roy G. Bryan, 5836 Long Brake Trail, Edina, Minn. 55436; Rollyn P. Lee, 1925 W. Oak St., Stillwater, Minn. 55082; Dale Gerasch, 7230 Riverdale Rd., Brooklyn Center, Minn. 55430

[21] Appl. No.: 08/833,946

[22] Filed: Apr. 14, 1997

Related U.S. Application Data

[63] Continuation-in-part of application No. 08/524,476, Sep. 7, 1995, abandoned.

[51] Int. Cl.[7] ............................................. A61B 5/00
[52] U.S. Cl. ............................................. 600/310
[58] Field of Search .................. 600/309, 310, 600/312, 322, 338, 339, 342, 345, 351, 361

[56] References Cited

U.S. PATENT DOCUMENTS

| | | |
|---|---|---|
| 3,224,433 | 12/1965 | Van Dalebor . |
| 3,959,107 | 5/1976 | Horner et al. . |
| 3,973,555 | 8/1976 | Möller et al. . |
| 4,200,110 | 4/1980 | Peterson et al. . |
| 4,244,375 | 1/1981 | Farrar et al. . |
| 4,281,659 | 8/1981 | Farrar et al. . |
| 4,294,258 | 10/1981 | Bernard . |
| 4,320,764 | 3/1982 | Hon . |
| 4,321,931 | 3/1982 | Hon . |
| 4,658,825 | 4/1987 | Hochberg et al. . |
| 5,150,709 | 9/1992 | Neward . |
| 5,361,757 | 11/1994 | Smith et al. ............................. 600/310 |
| 5,417,662 | 5/1995 | Hjertman et al. . |
| 5,529,064 | 6/1996 | Rall et al. ............................... 600/338 |
| 5,746,217 | 5/1998 | Erickson et al. ..................... 600/310 X |

FOREIGN PATENT DOCUMENTS

WO 91/18549  12/1991  WIPO .

OTHER PUBLICATIONS

Optical Sensor Incorporated article from Piper Jaffray, May 1995.

*Primary Examiner*—Samuel G. Gilbert
*Attorney, Agent, or Firm*—Faegre & Benson, LLP.

[57] ABSTRACT

A medical instrument which permits the continuous monitoring of fetal ECG and intermittent monitoring of fetal scalp blood pH during labor and delivery. The instrument includes (i) an electrically conductive needle effective as an ECG electrode, (ii) a plurality of pH probes or a single reusable and rotatable pH probe, (iii) a system for flushing the area around the pH probe prior to sampling, and (iv) a sharp proximate each probe for producing an extracorporeal fetal scalp blood sample to be measured.

13 Claims, 6 Drawing Sheets

INSTRUMENT FOR CONTINUOUSLY MONITORING FETAL HEART RATE AND INTERMITTENTLY MONITORING FETAL BLOOD PH AND METHOD OF USE

This is a continuation-in-part application of U.S. patent application Ser. No. 08/524,476, filed Sep. 7, 1995 now abandoned.

FIELD OF THE INVENTION

The invention broadly relates to instrument for monitoring signs of fetal distress during labor and delivery and methods of employing such probes. More specifically, the invention relates to instruments for monitoring fetal heart rate (ECG) and fetal blood pH and associated methods of employing such instruments.

BACKGROUND

Fetal heart action is commonly monitored during labor and delivery. Dramatic changes in fetal ECG measurements are generally indicative of fetal distress. A variety of ECG probes have been designed which are inserted through the vagina and cervix of the mother and attached to the epidermis of the fetus. Only physical contact between an electrode and the fetus is necessary to obtain good ECG readings. Typical ECG probes include an electrically conductive spiral needle which is subcutaneously introduced into the fetal scalp at one end and electrically connected to an amplifier and a cardiotachometer (i.e., an electrocardiograph) at the other end for measuring and recording the electrical impulses which initiate contraction of the heart.

Several such ECG probes are described in U.S. Pat. No. 4,244,375 (issued to Farrar et al.), U.S. Pat. No. 4,321,931 (issued to Hon) and U.S. Pat. No. 5,150,709 (issued to Neward). Such probes are well known and widely used in the medical profession.

Fetal blood pH is also commonly monitored during labor and delivery. Fetal blood pH is a well known measure of the metabolic and respiratory status of a fetus. The pH of fetal blood is dependent in large measure upon the concentration of carbon dioxide and acid in the blood, with an increase in carbon dioxide and/or acid producing a corresponding decrease in pH. A decrease in pH values suggests that the concentration of carbon dioxide in the fetal blood has increased, which is an early warning sign that the fetus is receiving insufficient oxygen. Monitoring of fetal blood pH is particularly useful for corroborating a diagnosis of fetal hypoxia based upon irregular fetal heart rate patterns.

A first type of pH probe utilizes a standard electrode cell assembly which includes a measuring electrode and a reference electrode. The construction of such pH probes is well known in the industry. The probe is subcutaneously introduced into the fetal scalp with the measuring electrode in contact with the biological fluid to be measured (generally blood). The measuring and reference electrodes are electrically connected to an amplifier and a recording device for measuring the electrical potential measured by the electrodes and recording those values as pH.

Several such electrode cell pH probes are described in U.S. Pat. No. 3,224,433 (issued to Von Dalebor), U.S. Pat. No. 3,959,107 (issued to Horner et al.), U.S. Pat. No. 3,973,555 (issued to Moller et al.), and U.S. Pat. No. 4,281,659 (issued to Farrar et al.). Such probes are well known and widely used in the medical profession.

A second type of pH probe utilizes optical fibers and a pH sensitive dye composition to measure pH. A first embodiment of such optical pH probes includes a pair of optical fibers are retained within an ion permeable envelope. A pH sensitive dye (i.e., a dye whose color intensity changes with changing pH values) is provided within the envelope. One of the optical fibers is connected to a light source for transmitting light into the envelope while the second optical fiber is connected to a light sensor for measuring the amount of light transmitted from the first optical fiber to the second optical fiber after passing through the pH sensitive dye composition. The measured light intensity can be directly correlated to pH based upon the known relationship between the color intensity of the pH sensitive dye composition and pH.

A second embodiment of such optical pH probes includes a single optical fiber containing a pH sensitive fluorescent dye in the distal end of the fiber. The proximal end of the optical fibers is connected to a light source for transmitting light of a known intensity down the fiber and into contact with the pH sensitive dye. The proximal end of the fiber is also attached to a light sensor for measuring the amount of light which is transmitted back up the optical fiber by the dye. The measured light intensity is dependent upon the extent to which the dye is able to absorb and fluoresce, a characteristic which can be directly correlated to pH based upon the known relationship between the fluorescent capacity of the dye and pH.

A fiber optic pH probe of the latter type is manufactured and sold commercially by several suppliers, including Ensign-Bickford Optics Company of Avon Connecticut.

Several attempts have been made to combine an ECG probe and a pH probe in a single device. Examples of such efforts are disclosed in U.S. Pat. No. 4,294,258 (issued to Bernard), U.S. Pat. No. 4,658,825 (issued to Hochberg et al.), and U.S. Pat. No. 4,320,764 (issued to Hon). Exemplary of these combination devices, the device disclosed by Hochberg et al. incorporates a fiber optic pH probe within the lumen of a typical electrically conductive spiral needle so that both the ECG probe (the needle) and the pH probe are subcutaneously positioned into contact with fetal interstitial tissue and fluids with a single puncture site for continuous in-vivo monitoring of ECG and fetal pH.

While the combination devices disclosed by Bernard, Hochberg et al. and Hon constitute a significant advance over the rather cumbersome and invasive technique of inserting and attaching multiple devices in order to monitor heart rate and pH, they have not been widely used within the medical field as they tend to suffer from a gradual loss of accuracy in pH measurement. It is believed that such loss of accuracy is due to the static nature of the probes relative to fetal tissue and fluids and the gradual dampening of normal biological ionic interchange at the incision cite.

Hence, research continues in an effort to develop a fetal ECG and pH monitoring device which is simple to use, reliable and provides accurate pH readings over extended periods of time.

SUMMARY OF THE INVENTION

We have discovered a medical instrument and associated method of use which provides continuous electrical and permits intermittent chemical monitoring of a fetus during labor and delivery. In a first embodiment, the instrument includes an electrically conductive needle which is effective as an ECG electrode, a plurality of spatially segregated pH probes, a remotely operable sharp for independently generating fetal blood samples proximate each pH probe, and a means for flushing the sampling site prior to the drawing of each fetal blood sample. The needle, pH probe(s) and sharp can be conveniently retained in proper operational position by a manifold base. The pH probes can be of any type capable of providing accurate and intermittent in vivo indications of pH, including the electrode cell and fiber optic types discussed previously. The needle and pH probes are connected to appropriate monitoring equipment, after attachment to the fetus, for continuously measuring and displaying fetal heart rate and intermittently measuring fetal blood pH as desired. The needle would generally be connected to a standard electrocardiograph. The pH probe(s) would be connected to either electrical monitoring equipment when pH is being measured by the electrical potential sensed by electrodes (electrode cell type probe) or light intensity monitoring equipment when pH is being measured by the color intensity of a pH indicator dye composition (fiber optic type probe).

In a second embodiment, the instrument includes a single repositionable and reusable pH probe which can be moved to different locations on the fetal scalp for purposes of allowing the intermittent testing of several different fetal blood samples without inserting and attaching an entire new device.

Another aspect of the invention relates to a method of continuously monitoring the heart rate and intermittently measuring the blood pH of a fetus. First, the instrument described above is attached to the scalp of a fetus, wherein the electrically conductive needle is in electrical sensing communication with the fetus. The fetal heart rate is continuously monitored. The sampling area between the instrument and the scalp is flushed with a biologically compatible solution. A fetal blood sample is produced within the sampling area with a sharp. The pH of the sample is measured with one of the pH probes. The steps of flushing the sampling area, producing a blood sample, and measuring the pH are intermittently repeated with one of the other pH probes of the instrument.

Another aspect of the invention relates to an instrument for measuring a fetal scalp blood parameter of a fetal scalp sample site. The instrument includes a housing having a top end, a bottom end, and a lumen extending from the bottom end toward the top end. The bottom end is adapted to be placed proximal to the fetal scalp sample site. The instrument also includes a probe having an end adapted for measuring the blood parameter. The probe is housed in the lumen such that the measuring end of the probe is positioned proximal to the bottom end of the housing. The instrument further includes a sharp, which is extendible from the housing on demand to an extended position for producing a fetal scalp blood sample. The sharp is also retractable into the housing to a retracted position after the blood sample is produced. The lumen of the housing is configured such that the blood sample produced by the sharp is capable of being drawn into the lumen and into engagement with the measuring end of the probe to allow the blood parameter to be measured.

Another aspect, the present invention relates to a method of measuring a fetal scalp blood parameter of a fetal scalp sampling site. According to the method, the instrument discussed immediately above is provided. The instrument is placed onto the fetal scalp sample site such that the bottom end of the housing is proximal to the fetal scalp sample site. The sharp is extended on demand to produce a blood sample. The sharp is retracted. The blood sample is drawn into the lumen of the housing and into contact with the measuring end of the probe to allow the blood parameter to be measured.

DETAILED DESCRIPTION OF THE
INVENTION INCLUDING A BEST MODE

Nomenclature
10 Instrument
11 Proximal End of Instrument
12 Distal End of Instrument
20 Base Element
21 Proximal End of Base Element
22 Distal End of Base Element
23 External Threads on Base Element
24 Peripheral Surface of Base Element
25 ECG Wire Passage
26 pH Probe Passage
27 pH Probe Passage
30 Retention Ring
31 Proximal End of Retention Ring
32 Distal End of Retention Ring
33 Dimple
34 Biased Sphere
35 Base Element Drive Shaft
40 Delivery Tube
43 Internal Threads on Delivery Tube
50 Helical Needle
51 Proximal End of Helical Needle
52 Distal End of Helical Needle
61 Measuring (Primary) ECG Electrode 62 Reference (Secondary) ECG Electrode
65 First ECG Electrical Wire
66 Second ECG Electrical Wire
70 Electrocardiograph monitor
80 pH Probe
81 Proximal End of pH Probe
82 Distal End of pH Probe
91 First Optical Fiber
92 Second Optical Fiber
100 pH Sensitive Indicator Dye Composition
110 Hydrogen Ion Permeable Receptacle
111 Wall of Ion Permeable Receptacle
171 Light Source
172 Light Sensor
180 Telescoping Collar
181 Proximal End of Collar
182 Distal End of Collar
190 Hollow Needle
191 Proximal End of Hollow Needle
192 Distal End of Hollow Needle
193 Terminal Point of Hollow Needle
195 Lumen Defined by Hollow Needle
196 Inwardly Extending Flange
210 Sharp Actuator Wire
211 Proximal End of Sharp Actuator Wire
212 Distal End of Sharp Actuator Wire
220 Sharp Actuating Mechanism
221 Knob
222 Wing
223 Biasing Spring
250 Protective Covering
251 Live Hinge
260 Flush Line
261 Proximal End of Flush Line
262 Distal End of Flush Line
265 Lumen of Flush Line
300 Instrument
301 Fetal Scalp Sample Site
302 Housing
304 Top End
306 Bottom End
307 Outward Flare
310 Blood Probe and Sharp Assembly
312 Inner Housing
314 Slideable Collar
316 Probe
318 Sharp
320 Actuator Wire
322 Top End
324 Bottom End
326 Lumen
328 Base Chamber
330 Axial Passage
332 End
334 Through Bore
338 Through Bore
340 Knob
342 Spring
344 Wings
Construction An electrically conductive helical needle 50, generally constructed of surgical grade stainless steel, extends from the distal end 22 of the base element 20 for rotational penetration into the epidermis of a fetus (not shown). The needle 50 functions as a primary electrode 61 in direct physical contact with a fetus (not shown). A secondary electrode 62 is also attached to the base element 20 but does not contact the fetus (not shown) for purposes of providing a reference signal for comparison purposes. Electrical wires 65 and 66 are connected to the proximal end 51 of the needle 50 and the secondary electrode 62, respectively. The wires 65 and 66 extend through a delivery tube 40 for connection to a remotely located electrocardiograph 70.

Other needle 50 configurations may be employed, such as that shown in U.S. Pat. No. 4,294,258, with the helical shape generally preferred because of the stability which it contributes to maintaining the position of the instrument 10 on the scalp of a fetus.

Any of a variety of mechanisms can be employed to provide rotational movement of the needle 50 from a location external to the uterus (not shown). Two such mechanisms are shown in U.S. Pat. Nos. 4,320,764 and 4,321,931. The mechanism shown in U.S. Pat. No. 4,320,764 provides a slot in the delivery tube and a corresponding tab extending from the base element whereby rotation of the delivery tube is transmitted to the base element, and thereby to the needle, when the tab is engaged within the slot. The mechanism shown in U.S. Pat. No. 4,321,931 employs a needle embedded within a plunger which is threadably engaged within a delivery tube, such that linear motion of the plunger relative to the delivery tube is translated into a spiral movement of the needle.

As shown in FIGS. 1 through 4, a first embodiment of the instrument 10 includes a plurality of passages 26 and 27 for housing pH probes 80 provided within the base element 20. The embodiment shown in FIGS. 1 through 4 has two equidistantly spaced passages 26 and 27 on opposite sides of the electrically conductive helical needle 50. Each pH probe 80 housed in passages 26 and 27 can provide accurate measurements of fetal pH for a limited period of time with the accuracy of the reading deteriorating fairly quickly due primarily to contamination of the blood sample (not shown). Generally, fairly accurate pH readings can be obtained for about 5 to about 20 minutes after each incision.

Any number of pH probes 80 can be provided in the first embodiment, dictated by size and cost constraints. Generally, about two to five pH probes 80 provide sufficient pH testing capacity and result in an acceptably sized base element 20. The pH probes 80 can be of the standard electrode cell type (not shown) or the fiber optic type (shown in FIGS. 1–9).

Figure 5:
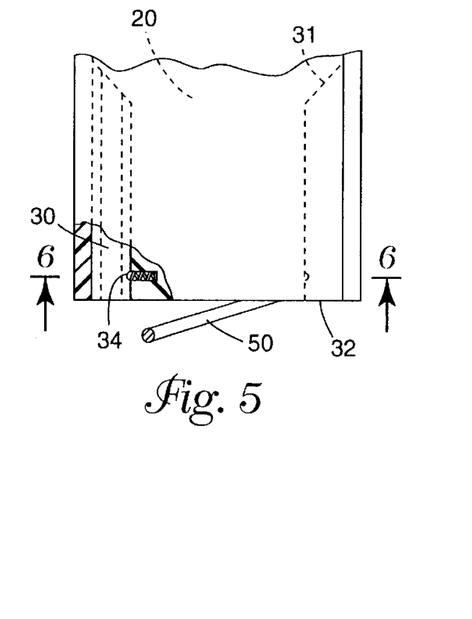
FIG. 5 is a side-view of a second embodiment of the invention with a portion thereof broken away to reveal internal elements.
Figure 6:
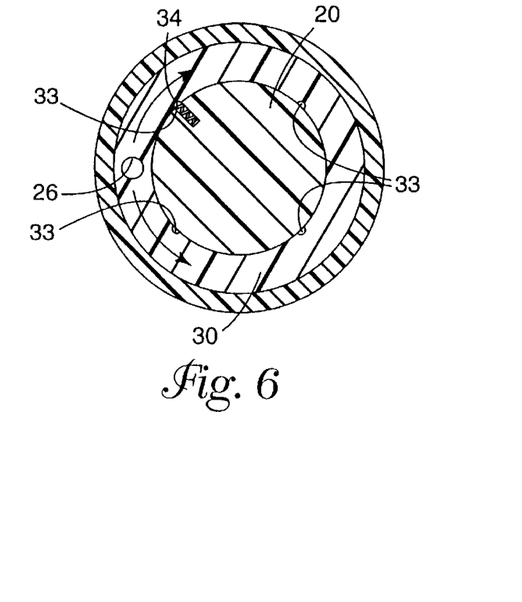
FIG. 6 is a front view of the invention depicted in FIG. 5.

A second embodiment of the instrument 10 shown in FIGS. 5 and 6 includes a single repositionable pH probe 80 housed within passage 26 of base element 20. The repositionable pH probe 80 is rotatable about the helical needle 50 to different sampling sites (not shown). Rotation of the pH probe 80 must be provided in such a manner that (i) rotation of the pH probe 80 does not inherently cause rotation of the helical needle 50 implanted into the fetal scalp 500, and (ii) the pH probe 80 can be sequentially secured into position at predetermined sampling sites for purposes of ensuring maximal spacing between incisions (not shown) and preventing overlapping incisions (not shown). In addition, the mechanism used to achieve rotational movement of the pH probe 80 is preferably a simple, inexpensive and substantially self-operating device requiring limited user knowledge or skill to operate.

A sample of such a mechanism is depicted in FIGS. 5 and 6 in which the pH probe 80 is retained within a rotatable annular retention ring 30 surrounding the base element 20, with the retention ring 30 rotated by turning a retention ring drive shaft (not shown) and positioning of the retention ring 30 at a suitable sampling site (not shown). As shown in FIG. 6, proper positioning of the pH probe 80 at the next sampling site (not shown) can be indicated by increased resistance to further rotation of the retention ring 30 due to the forced extension of an outwardly biased sphere 34 retained along the peripheral surface 24 of the base element 20 into a corresponding dimple 33 in the retention ring 30. Proper rotational positioning of the retention ring 30 at a suitable sampling site (not shown) could also be indicated electrically (e.g., the closing of an open electrical circuit (not shown) only when the retention ring 30 is in the proper position).

Those skilled in the art could construct numerous alternative electrical and mechanical embodiments capable of achieving the design and performance characteristics outlined herein for the repositioning mechanism. For example, the repositionable aspect could also be achieved by the incorporation of multiple pH probe retention channels (not shown) in the base element 20 at each desired sampling site (not shown) with an accompanying conduit (not shown), such as separate flush lines 260, extending from each retention channel (not shown). The conduits (not shown) would extend a distance sufficient to allow medical personnel (not shown) to remove the pH probe 80 from one retention channel (not shown) and insert the withdrawn probe 80 into another of the retention channels (not shown). The specific embodiments shown and described herein are provided for illustrative purposes only and are not intended to unduly limit the scope of the invention.

The construction and use of pH electrode cells for use in the monitoring of fetal pH are well known and therefore are not depicted in the accompanying drawings. Standard pH electrode cells include a reference electrode cell and a measuring electrode cell. The reference electrode cell is formed by immersing a silver-silver chloride electrode in an electrolytic solution retained within a glass tube. A typical electrolytic solution is a saturated aqueous salt solution. The distal end of the glass tube is covered with an ion permeable membrane which allows for the free transfer of ions between the electrolytic solution and a test solution and thereby prevents the development of an electrical potential across the membrane. Hence, an electrical potential is generated within the reference electrode cell only at the interface of the silver-silver chloride electrode and the electrolyte solution. This potential is the reference potential.

The measuring electrode cell is similarly formed by immersing a silver-silver chloride electrode in an electrolytic solution retained within a glass tube. However, the distal end of the glass tube is covered with a membrane which is permeable only to hydrogen ions. Hence, the measuring electrode cell develops an electrical potential (i) at the interface of the silver-silver chloride electrode and electrolyte solution, and (ii) across the membrane. The electrode/electrolyte potential developed in the measuring electrode cell should be equal to the electrode/electrolyte potential developed in the reference electrode cell. The membrane potential correlates to the relative concentrations of hydrogen ions in the electrolyte solution and the test solution and is therefore a measure of the acidity of the test solution.

The reference and measuring potential detected by the corresponding electrodes are applied in opposition across a variable resistive element. This cancels the electrode/electrolyte potentials detected by each of the electrodes. A potentiometer and a voltmeter measure the voltage of the remaining potential generated across the membrane in the measuring electrode cell with the magnitude of the voltage translated into pH.

Figure 7:
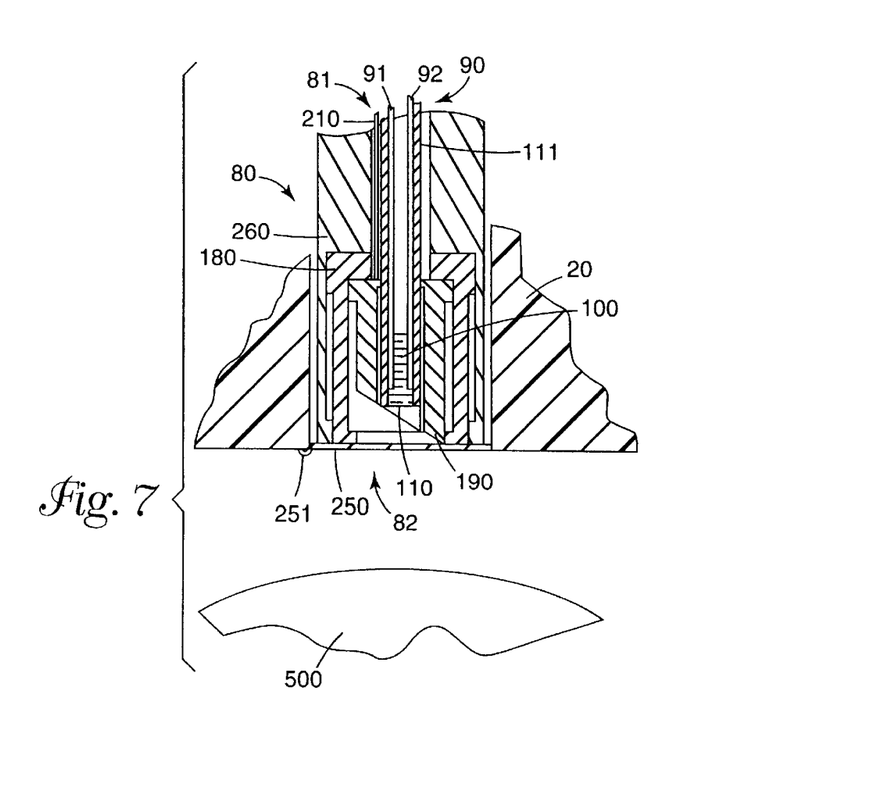
FIG. 7 is a cross-sectional side view of one embodiment of a dual filament pH probe prior to activation of the sharp and collar.
Figure 8:
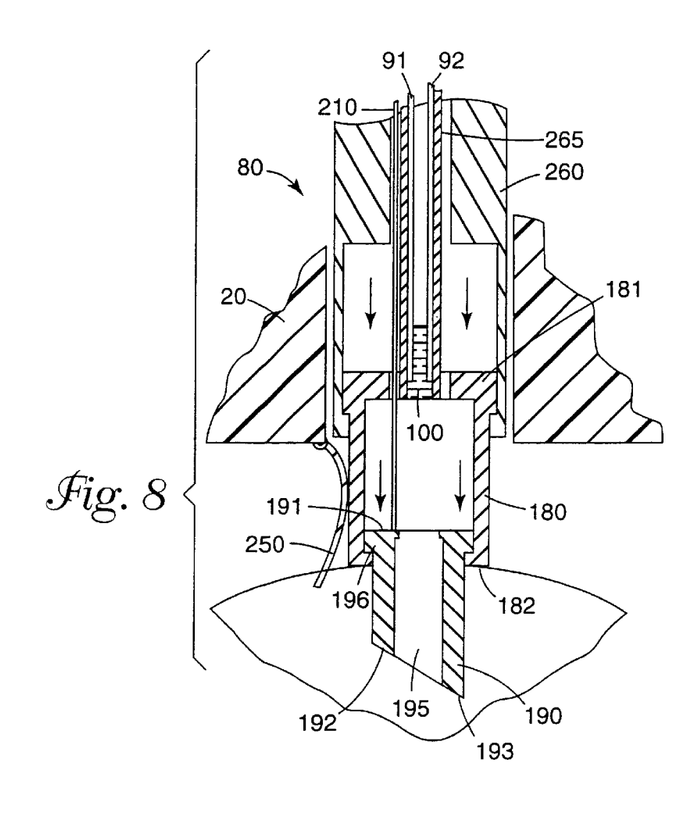
FIG. 8 is a cross-sectional side view of the dual filament pH probe shown in FIG. 7 with the sharp and collar extended toward the scalp of a fetus.
Figure 9:
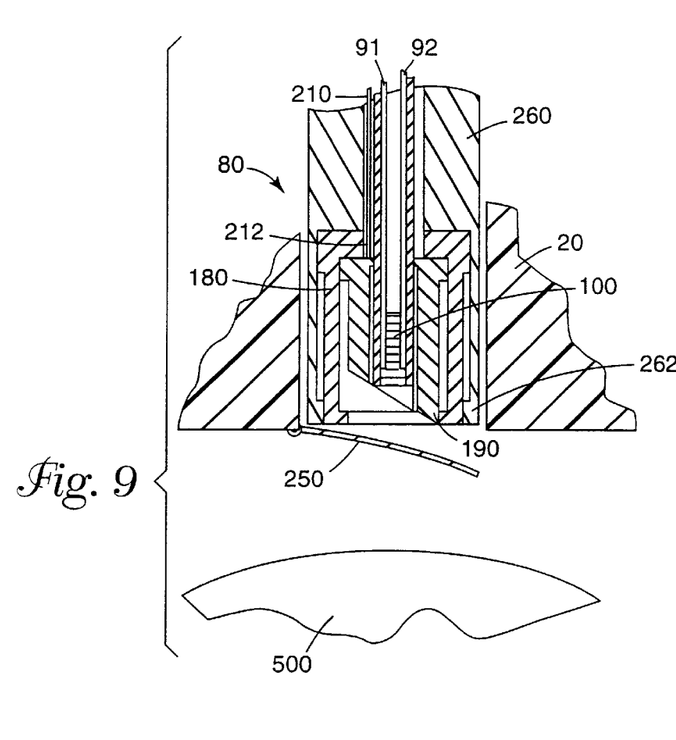
FIG. 9 is a cross-sectional side view of the dual filament pH probe shown in FIGS. 7 and 8 with the sharp and collar retracted into the base.

Similarly, the construction and use of fiber optic pH probes are well known. As shown in FIGS. 7–9, one common type of fiber optic pH probe 80 includes a pair of optical fibers 91 and 92 immersed in a pH sensitive indicator dye composition 100 retained within an ion permeable receptacle 110. The pH sensitive indicator dye composition 100 is a dye whose color intensity changes with changing pH values. As shown best in FIG. 11, the first optical fiber 91 is connected to a light source 171 for transmitting light along the optical fiber 91 and into the pH sensitive indicator dye composition 100. The second optical fiber 92 is connected to a light sensor 172 for measuring the amount of light transmitted through the pH sensitive indicator dye composition 100 from the first optical fiber 91 to the second optical fiber 92.

Immersion of the receptacle 110 into a test sample (not shown) results in the migration of hydrogen ions between the test solution (not shown) and the pH sensitive indicator dye composition 100 through the wall of the receptacle 111. The color intensity of the pH sensitive indicator dye composition 100 changes in accordance with the pH of the test sample (not shown). This allows for the determination of test sample pH by simply measuring the color intensity (i.e., the extent to which light is absorbed) of the pH sensitive indicator dye composition 100.

Embodiments of a fiber optic pH probe suitable for use in the instrument 10 as probe 80 is disclosed in U.S. Pat. No. 4,200,110 (issued to Peterson et al.), which disclosure is hereby incorporated by reference.

Figure 12:
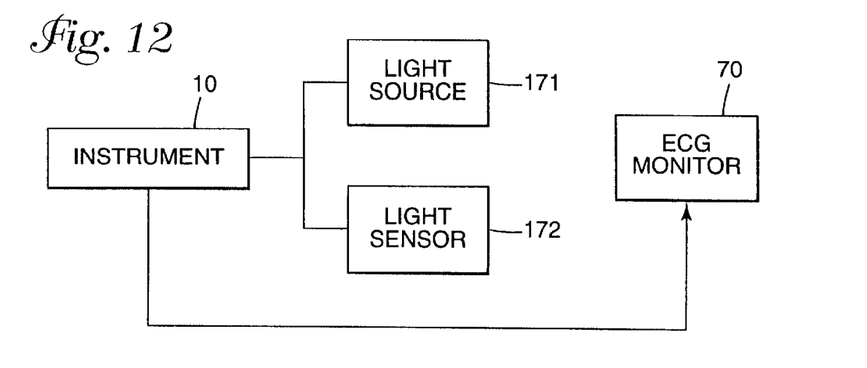
FIG. 12 is a schematic diagram of the monitoring equipment used with a single fiber optic embodiment of the invention.

Referring to FIG. 12, another common type of configuration of a fiber optic pH probe suitable in the practice of the invention includes a single optical fiber containing a pH sensitive indicator dye composition entrapped within the optical fiber at the distal end of the fiber. The pH sensitive indicator dye composition is a dye whose fluorescent capacity changes with changing pH values. The proximal end of the optical fiber would be connected to a light source 171 for transmitting a short burst of light along the optical fiber and into contact with the pH sensitive indicator dye composition at the distal end of the fiber for causing the dye composition to absorb the light energy and fluoresce. A light sensor 172 is also connected to the proximal end of the fiber for measuring the amount of fluorescent light transmitted back-up through the fiber by the dye composition.

Immersing the distal end of the fiber into a test sample results in the migration of hydrogen ions into the interstitial void volume within the optical fiber and into contact with the pH sensitive indicator dye composition retained within the fiber. The color intensity and fluorescent capacity of the pH sensitive indicator dye composition changes in accordance with the pH of the test sample. This allows for the determination of test sample pH by simply measuring the extent to which the dye composition emits fluorescent light energy after being subjected to a known level of energizing light.

Single strand fiber optic pH probes suitable for use in the instrument 10 are manufactured by several fiber optic manufacturers.

Referring now mainly to FIGS. 7–9, a sharp effective for piercing the skin 500 and producing a blood sample (not shown) is provided proximate each pH probe 80. The sharp of FIGS. 7–9 is in the form of a hollow needle 190 configured and arranged to slideably accommodate the pH probe 80 within the lumen 195 of the needle 190. The distal end 192 of the needle 190 is tapered for facilitating penetration of the needle 190 into fetal tissue 500. The proximal end 191 of the needle 190 is firmly attached to the distal end 212 of an actuator wire 210. The actuator wire 210 is retained within the lumen 265 of flexible flush line 260. Both the wire 210 and flush line 260 extend completely through the delivery tube 40 where they are accessible to medical personnel (not shown).

The distal end 262 of the flush line 260 is attached to the base element 20. The proximal end 211 of the actuating wire 210 extends beyond the proximal end 601 of the flush line 260 and is connected to a knob 221. A pair of wings 222 extend radially from the flush line 260 near the proximal end 261 of the flush line 260. The actuator wire 210 may be linearly reciprocated, so as to extend the hollow needle 190 towards the fetus 500, by gripping the wings 222 with the pointer and middle fingers (not shown) and pressing the knob 221 with the thumb (not shown) towards the wings 222. A biasing spring 223 is provided between the knob 221 and the flush line 260 for biasing the actuator wire 210 towards its original retracted position relative to the flush line 260 upon removal of actuating pressure from the knob 221.

An outwardly extending flange 196 is provided at the distal end 192 of the hollow needle 190 for cooperatively engaging the distal end 182 of the collar 180 as the needle 190 is advanced towards the fetus 500. Once engaged by the flange 196, the collar 180 is carried towards the fetus 500 along with the needle 190. The needle 190 is extended until the needle penetrates into fetal tissue 500 and a blood sample (not shown) is produced. The distal end 182 of the collar 180 is linearly offset from the distal end 192 of the needle 190 a distance sufficient to allow the needle 190 to penetrate into fetal tissue 500 while the pH probe 80 remains extracorporeal relative to fetal tissue 500. The needle 190 is then automatically retracted back to its original retracted position by spring 223. This leaves the pH probe 80 in proper position, proximate the incision (not shown) made by the needle 190, for contacting the blood sample (not shown) and providing an accurate measure of fetal blood pH.

Collar 180 thus helps to ensure that the incision provided by actuation of the needle 190 consistently results in the sampling of fetal scalp blood rather than maternal blood (incision too shallow) or subcutaneous fetal fluid (incision too deep). The collar 180 is automatically retracted back to its original retracted position along with needle 190 by spring 223.

The depth of the incision (not shown) is fairly important to ensure accurate pH readings. The sampling of maternal blood simply provides a false reading as the pH of maternal blood cannot be correlated to the pH of fetal blood. The sampling of subcutaneous fluid from a fetus, while providing a fairly accurate reading of fetal blood pH, generally provides a historical reading of fetal blood pH as pH changes in the subcutaneous fluid of a fetus are significantly delayed relative to changes in the pH of fetal scalp blood.

Alternative configurations for providing a reciprocating sharp proximate each pH probe 80 which is effective for penetrating fetal tissue 500 and producing a blood sample (not shown) are within the scope of this invention. Examples of such alternative embodiments include, a scalpel blade (not shown) proximate each pH probe 80, and a single lance (not shown) rotatably retained within the base element 20 which can be rotatably repositioned proximate each pH probe 80.

Still referring to FIGS. 7–9, a flush line 260 extends completely through the delivery tube 40 with a distal end 262 extending through the base element 20 and terminating proximate the distal end 82 of each pH probe 80. The proximal end 261 of each flush line 260 projects out of the delivery tube 40 where they are accessible to medical personnel (not shown).

The proximal end 261 of each flush line 260 is connected to a source of a biologically acceptable flushing solution (not shown), such as saline. A plunger mechanism is provided to propel the flushing solution (not shown) down the flush line 260 and out the distal end 262 of the line 260 for cleansing the sampling area (not shown) between the distal end 82 of the pH probe 80 and the incision site (not shown).

As shown in FIGS. 7–9, the flush line 260 may conveniently be configured with the pH probe 80 positioned within the lumen 265 of the line 260. This would allow the distal end 262 of the flush line 260 to surround the periphery (unnumbered) of the distal end 82 of the pH probe 80 and conduct flushing solution (not shown) into direct contact with the distal end 82 of the pH probe 80.

The sharp actuating mechanism 220 used to actuate the hollow needle 190 could be configured to also provide the motive force for propelling flushing solution (not shown) down the flush line 260 with a single stroke effecting both procedures. Such a dual purpose actuating mechanism 220 would simplify use of the instrument 10, but must provide cleansing of the sampling area (not shown) with the flushing solution (not shown) prior to generation of the fetal scalp blood sample (not shown) by actuation of the hollow needle 190.

Referring now to FIGS. 1–4 and 7–9 collectively, base element 20 operably positions the helical needle 50, pH probes 80, hollow needle 190 and flushing lines 260. The helical needle 50 extends from and is fixedly attached to the distal end 22 of the base element 20. An ECG wire passage 25 extends through the base element 20 for accommodating attachment of a first electrical wire 65 to the proximal end 51 of the helical needle 50. A reference ECG electrode 62 is fixedly attached to the proximal end 21 of the base element 20 with a second ECG electrical wire 66 attached to the reference electrode 62.

Figures 1, 3:
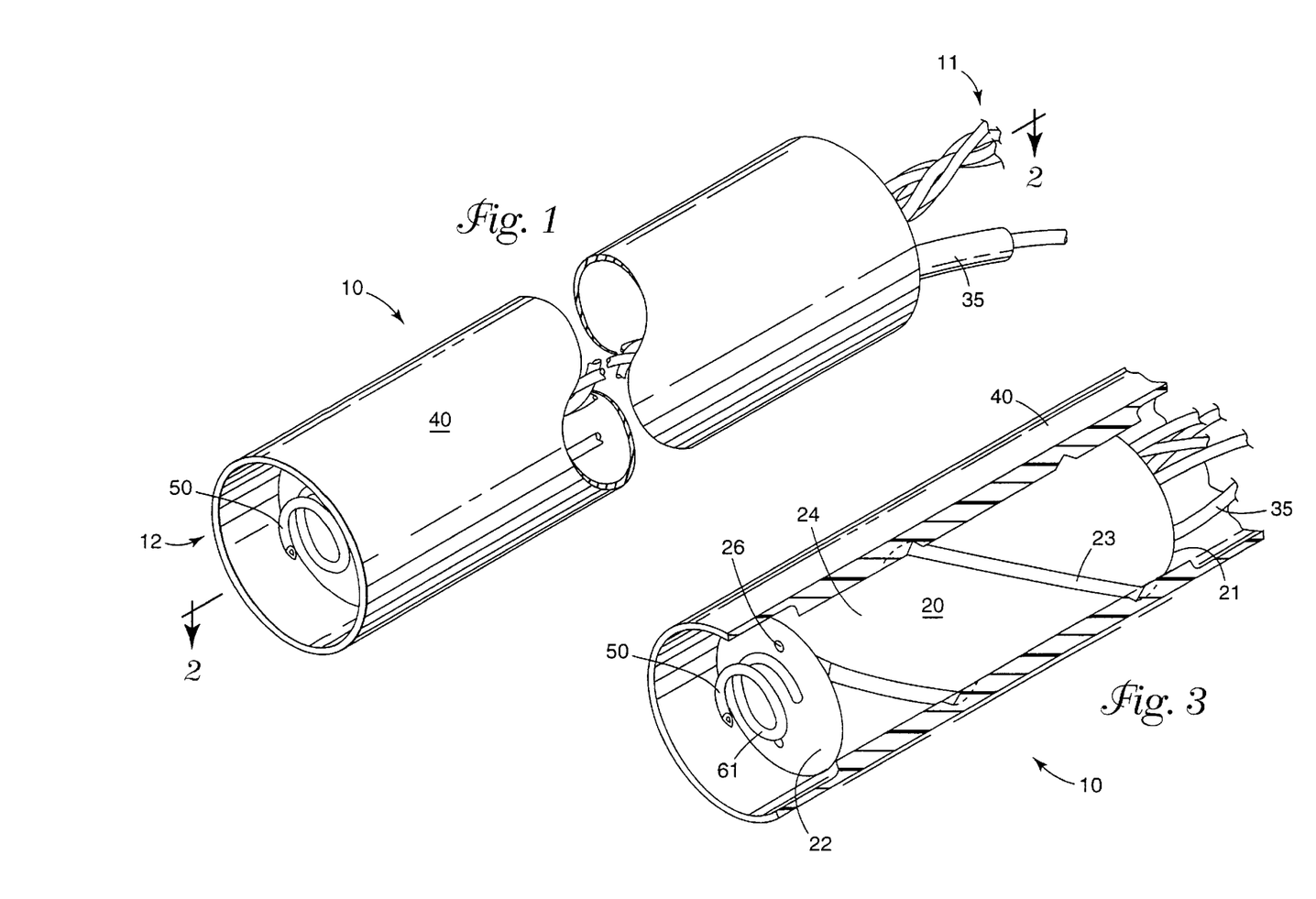
FIG. 1 is a perspective view of one embodiment of the present invention depicting multiple, single filament fiber optic pH sensors.
FIG. 3 is a perspective view of the invention depicted in FIG. 1 with a portion thereof broken away to reveal internal elements.
Figure 2:
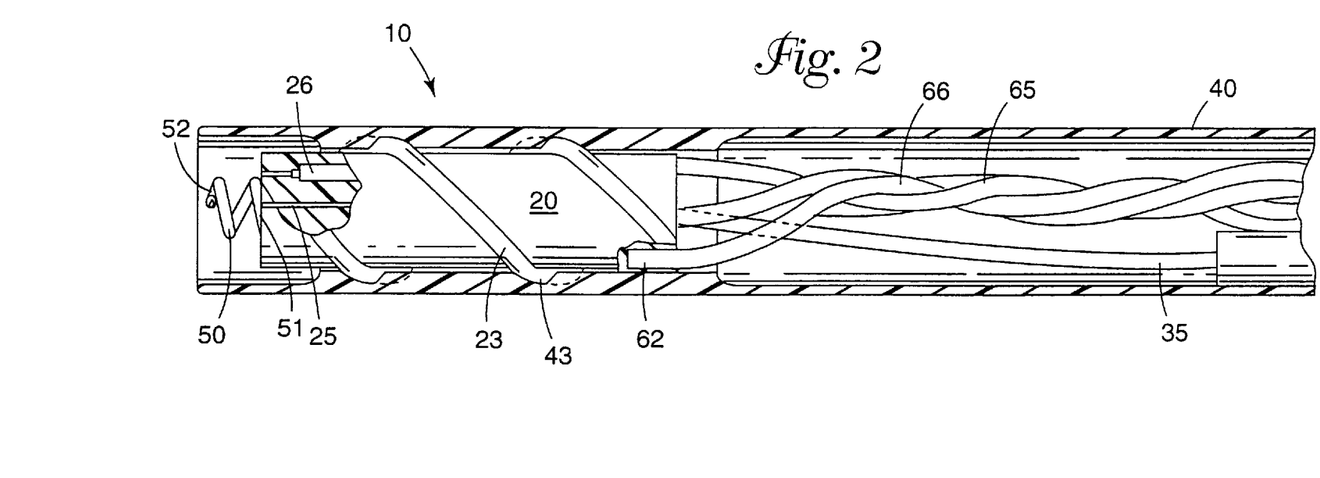
FIG. 2 is a cross-sectional side view of the invention depicted in FIG. 1 taken along line 2—2.
Figure 4:
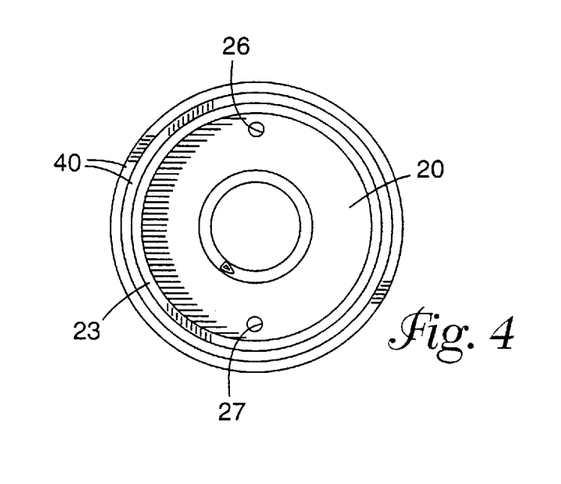
FIG. 4 is a front view of the invention depicted in FIG. 1.

As shown best in FIG. 4, the passages 26 and 27 housing pH probes 80, flush lines 260, and hollow needles 190, are equidistantly spaced encircling the helical needle 50. The passages 26 and 27 are equidistantly spaced for purposes of maximizing the distance between pH probes 80 and thereby minimizing the potential for contamination between blood samples (not shown). Each of passages 26 and 27 extend completely through the base element 20.

The base element 20 is rotatably attached to the delivery tube 40 by threaded engagement means such that linear force applied to the base element 20 relative to the delivery tube 40 is translated into spiral rotation of the base 20 element. The lead and pitch of the threaded base element 20 is designed to correspond with the lead and pitch of the helical needle 50 for providing smooth penetration of the helical needle 50 into the fetal tissue 500 with minimal tissue damage. One example of such a rotatably attached base element 20 is shown in U.S. Pat. No. 4,321,931 (issued to Hon), the disclosure of which is hereby incorporated by reference. A base element drive shaft 35 extends the length of the delivery tube 40 and is attached to the proximal end 21 of the base element 20 for allowing motive force to be remotely applied to the base element 20 by medical personnel (not shown).

Similarly, in the embodiment of FIGS. 5 and 6 utilizing a rotatable pH probe 80, a retention ring drive shaft (not shown) could extend the length of the delivery tube 40 and is attached to the proximal end 31 of the retention ring 30 for rotational force to be remotely applied to the retention ring 30 by medical personnel (not shown).

Referring now primarily to FIGS. 7–9, a protective covering 250 is provided over each of passages 26 and 27 in the base element 20 for preventing premature contact between the individual pH probes 80 and biological fluids (not shown). Suitable protective coverings 250 must be capable of ensuring the maintenance of a protective seal during normal attachment and use of the instrument 10 while permitting simple and reliable breaking of the seal by actuation of the hollow needle 190 and/or the pH probe 80 without fully detaching the covering 250 from the base element 20. The covering 250 is constructed of a thin plastic which is integrally fabricated with the base element 20 and provided with a live hinge 251 diametrically opposed along the perimeter of the covering 250 from the terminal point 193 of the hollow needle 190 for preventing complete detachment of the covering 250. However, typical protective coverings, such as covering 250 shown in FIGS. 7–9, would tend to prevent flushing of the sampling site (not shown) until the hollow needle 190 penetrates the seal 250. Alternative embodiments permitting sealing of the pH probe 80 without sealing the lumen (not shown) of the flush line 260 is also contemplated.

Figure 10:
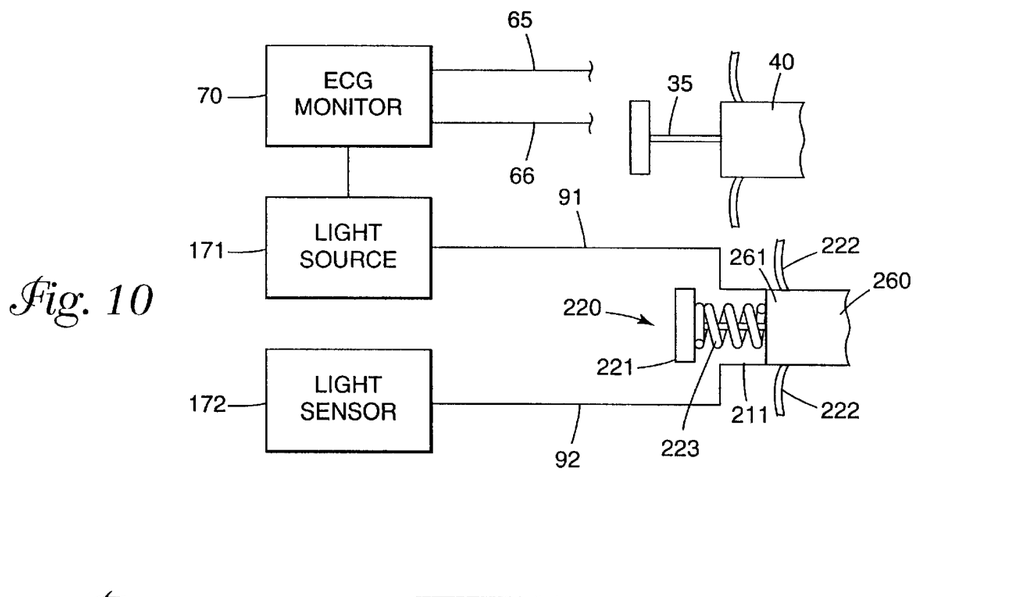
FIG. 10 is a schematic diagram of the external portions of the invention shown in FIGS. 7–8.
Figure 11:
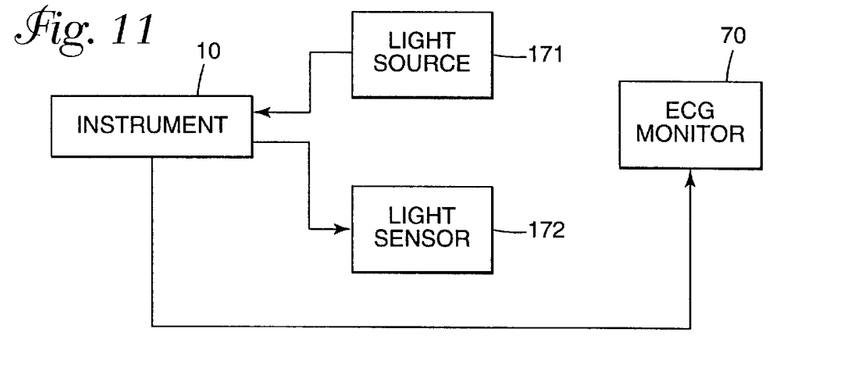
FIG. 11 is a schematic diagram of the monitoring equipment used with a dual fiber optic embodiment of the invention.

As shown in FIGS. 10–12, ECG electrical wires 65 and 66 are electrically connected to an electrocardiograph monitor 70 for measuring and recording the electrical impulses detected by the ECG electrodes 61 and 62 (FIG. 2) which initiate contraction of the heart.

As shown in FIG. 11, when dual fiber optic pH probes 90 are used, the paired optical fibers 91 and 92 within each pH probe 90 are connected to a light source 171 and a light sensor 172, respectively, for measuring and recording the color intensity of the pH sensitive indicator dye composition and translating such color intensity into pH.

Similarly, as shown in FIG. 12, when a single strand fiber optic pH probe is used, the single optical fiber is connected to both the light source 171 and light sensor 172 for measuring and recording the fluorescent intensity of the pH sensitive indicator dye composition and translating such intensity into pH.

When electrode cell pH probes are used, the measuring and reference electrodes are similarly electrically connected to appropriate monitoring equipment for measuring and recording the electrical potential across the corresponding cell membrane and translating this electrical potential into pH.

The procedure for attachment and use of the instrument 10 is substantially the same as that used with traditional ECG fetal probes. For example, still referring mainly to FIGS. 7–10, the ECG electrical wires 65 and 66, extending from the helical needle 50 and the reference electrode 96, are connected to an electrocardiograph monitor 70 for continuously monitoring fetal heart rate. The instrument 10 is attached to a fetus 500 during labor and delivery by inserting the distal end 12 of the instrument 10 through the vagina and cervix of the mother (not shown) and into contact with the scalp of the fetus 500. The helical needle 50 is attached to the fetus 500 by gripping the delivery tube 40 and depressing the base element drive shaft 35 towards the fetus 500.

The sampling site may be cleansed with flushing solution (not shown) and fetal blood pH measured with pH probe 80 by simply gripping the wings 222 extending from the flush line 260 and depressing the knob 221 at the proximal end 211 of the sharp actuating wire 210 towards the fetus 500. This procedure may be repeated intermittently as considered necessary and appropriate for ensuring accurate and timely pH measurements by either (i) repeating the procedure with one of the other pH probes 80 when multiple pH probes 80 are provided, or (ii) rotating the pH probe 80 until it locks into the next sampling site (not shown) and repeating the procedure in those instances when the embodiment of FIGS. 5 and 6 if used.

Figure 13:
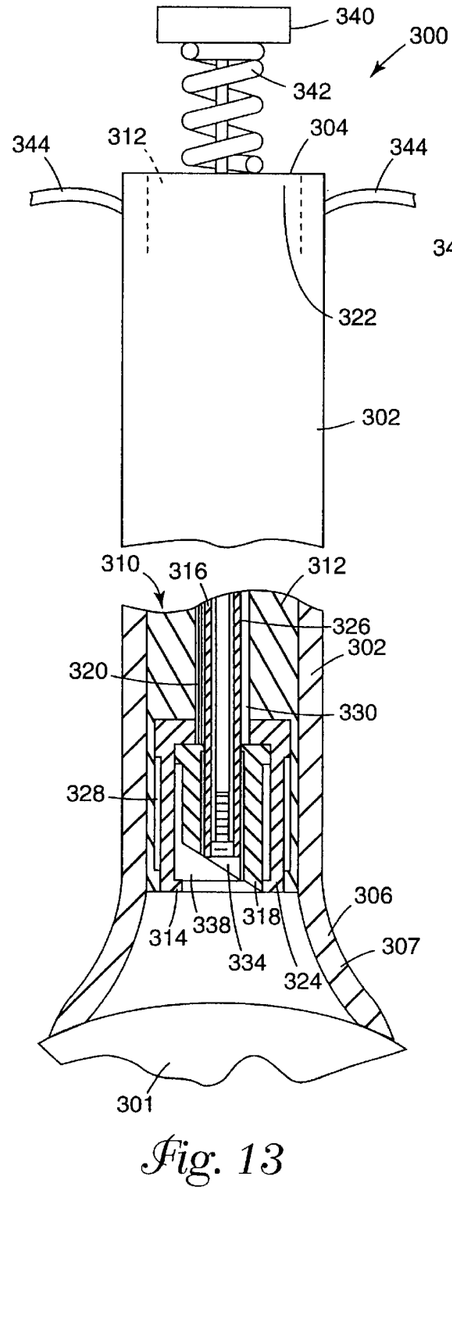
FIG. 13 is a side view of an alternative embodiment of the invention partially in cross section to show the collar and sharp in retracted prsitions.
Figure 14:
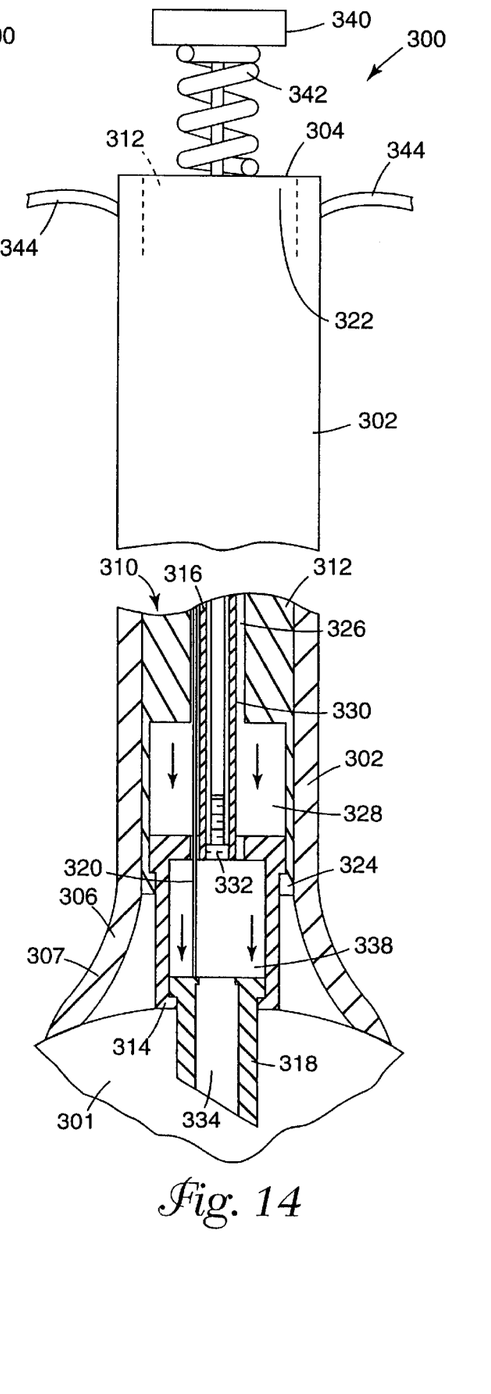
FIG. 14 is a side view of the embodiment of FIG. 13 partially in cross section to show the collar and sharp in extended positions.

FIGS. 13 and 14 show an alternative embodiment of an instrument 300 for measuring a fetal scalp blood parameter at a fetal scalp sample site 301. Instrument 300 includes outer housing 302 having a top end 304 and a bottom end 306. Bottom end 306 is provided with an outward flare 307 which facilitates placement of instrument 300 onto fetal scalp sample site 301 in multiple ways. Firstly, the outward flare 307 provides a surface against which fingertip pressure can be applied to help hold instrument 300 in place. Additionally, the outward flare 307 forms a suction cup shape to enhance suction between instrument 300 and fetal scalp sample site 301 when a suction force is applied, if desired, to help hold instrument 300 in place.

Instrument 300 further includes blood probe and sharp assembly generally designated as 310, which includes inner housing 312, slideable collar 314, probe 316, sharp 318, and actuator wire 320. Inner housing 312 includes a top end 322 and bottom end 324. Lumen 326 extends through inner housing 312 and is formed with base chamber 328 located proximal bottom end 324 and axial passage 330 extending from base chamber 328 to top end 322. Inner housing 312 is shown as a separate part from outer housing 302, but the two housings could be integrally formed as a single, unitary piece if desired.

Probe 316 includes an end 332 adapted for measuring one or more blood parameters of interest, such as blood pH, $pO_2$, $pCO_2$, glucose, K values, Na, urea, and the like. Probe 316 as shown is positioned in lumen 326 such that measuring end 332 extends into base chamber 328 proximal to the fetal scalp sampling site 301. In this position, a blood sample produced by instrument 300 is easily drawn into contact with measuring end 332 by capillary action. Probe 316 can have any configuration known in the art to be suitable for measuring the blood parameter of interest, and the present invention is not limited to any particular design. For example, probe 316 could be in the form of a pH electrode cell, a double strand fiber optic probe, or a single strand fiber optic probe as described above. In the particular embodiment of FIGS. 13 and 14, probe 316 is in the form of a double strand fiber optic probe.

Sharp 318 is generally supported in base chamber 328 and is capable of reciprocating, slideable movement between a fully retracted position as shown in FIG. 13 to a fully extended position as shown in FIG. 14. Preferably, in the fully extended position, sharp 318 extends to a position effective for making a scalp capillary depth incision to ensure that the blood sample is produced from fetal scalp capillaries rather than from interstitial fluids present at greater depths. Advantageously, making such a shallow incision in which the blood sample is drawn from scalp capillaries provides excellent characterization of actual blood parameters. This is possible because the fetal scalp capillaries are in relatively rapid equilibrium with the main fetal blood supply. Thus, blood parameters measured from fetal scalp capillaries generally correlate quite well with corresponding blood parameters in the main blood supply, and such parameters are very useful for monitoring fetal distress. In contrast, blood samples obtained from deeper, interstitial tissues are in slow equilibrium with the fetal blood. As a result, measurements of blood parameters taken from such interstitial sites tend to correlate poorly with actual blood parameters. These values are not as effective for monitoring fetal distress.

Advantageously, sharp 318 is extendable and retractable to produce blood samples upon demand. This allows fresh samples to be obtained as often as desired from multiple sampling sites and further allows intermittent sampling at desired testing intervals. In contrast, with some previously known devices, blood samples are only obtainable at a single sampling site over a long period of time such that the sampling site goes stale and good equilibrium with the main blood supply is lost. The ability to extend and retract the sharp 318 upon demand also allows the instrument 300 to be placed into position first with the sharp 318 retracted, only after which sharp 318 is then extended to make an incision. This is desirable for safety reasons in that the mother and fetus are protected against accidental incisions while the sharp 318 is retracted.

Sharp 318 is provided with through bore 334 which serves multiple functions. First, through bore 334 slideably receives probe 316 as the sharp is transported between the retracted position as shown in FIG. 13 and the extended position as shown in FIG. 14. Second, through bore 334 provides a passage for the blood sample to be drawn by capillary action into contact with measuring end 332 of probe 316.

Collar 314 is also generally supported in base chamber 328 and is capable of reciprocating, slideable movement between a fully retracted position as shown in FIG. 13 to a fully extended position as shown in FIG. 14. Collar 314 helps slidingly couple sharp 318 to inner housing 312. Collar 314 includes through bore 338 which serves multiple functions. First, through bore 338 slideably receives both probe 316 and sharp 318 as collar 314 is transported between its retracted and extended positions. Second, through bore 338 provides a passage for the blood sample to be drawn by capillary action into contact with measuring end 332 of probe 316. Third, collar 314 helps limit the extent to which sharp 318 is able to extend from inner housing 312 when the sharp 318 is in its extended position shown in FIG. 14.

Sharp 318 is coupled to knob 340 by actuator wire 320. Knob 340 is biased upward, and sharp 318 is biased toward the retracted position, by spring 342. Wings 344 extend from the sides of outer housing 302 near top end 304. Knob 340, spring 342, and wings 344 are useful for extending and retracting sharp 318. To cause sharp 318 to extend toward the fetal scalp sampling site 301 and produce a blood sample, wings 344 may be gripped with the middle fingers of one hand as knob 340 is pressed downward with the thumb. Downward movement of knob 340 causes actuator wire 320 to move downward as well and thereby cause sharp 318 to extend from inner housing 312 as shown in FIG. 14. To cause sharp 318 to retract, downward pressure on knob 340 is released. Spring 342 drives knob 340 upward, and this in turn pulls sharp 318 back to the retracted position as shown in FIG. 13.

According to a preferred mode of operation for measuring a blood parameter of interest, instrument 10 is provided in the retracted configuration shown in FIG. 13. Probe 316 is also coupled to a suitable apparatus so that measurements can be processed and outputted in useful form, e.g., on a printout and/or usually on a visual display. The instrument 10 is then placed against fetal scalp sampling site 301. Fingertip pressure against outward flare 307 can be used to help hold instrument 10 in place. Additionally, a suction force could be applied through lumen 326 in order to help hold instrument 10 in place, if desired. As instrument 10 is held in place against fetal scalp sampling site 301, site 301 can be flushed with a biocompatible solution through lumen 326 if desired. After the flush, knob 340 is depressed in order to extend sharp 318 as shown in FIG. 14 and make an incision to produce a blood sample. After the blood sample is produced, sharp 318 is retracted. The blood sample is then drawn into lumen 326 by capillary action where the blood sample contacts measuring end 332 of probe 316. The parameter of interest is then be measured. The measurement is communicated to the apparatus coupled to probe 316 from which the measured blood parameter is outputted. In the meantime, the suction holding instrument 300 onto site 301 is released, and instrument 300 is withdrawn until another reading is needed. The procedure may then be repeated with the same instrument 300, or a fresh instrument if desired. The embodiment shown in FIGS. 13 and 14 is thus advantageous because it allows blood parameters to be measured intermittently from fresh sample sites without having to first insert a fetal scalp electrode such as needle 50 shown in FIG. 1.

Other embodiments of this invention will be apparent to those skilled in the art upon consideration of the specification or from practice of the invention disclosed herein. Various omissions, modifications, and changes to the principles of the embodiments described herein may be made by one skilled in the art without departing from the true scope and spirit of the invention which is indicated by the following claims:

I claim:

1. A unitary instrument providing continuous electrical and intermittent chemical monitoring of a fetus, comprising:

(a) an electrically conductive needle;

(b) a plurality of spatially segregated pH probes; and (c) a remotely operable sharp for producing blood samples proximate each said probe.

2. The instrument of claim 1 wherein the electrically conductive needle, plurality of pH probes and sharp are operably configured and arranged within a manifold.

3. The instrument of claim 1 wherein the electrically conductive needle is an electrically conductive spiral needle capable of rotatable penetration into fetal scalp tissue.

4. The instrument of claim 1 wherein the pH probes are fiber optic pH probes, each of which comprises a single optical fiber having a pH sensitive dye indicator composition embedded within a distal end of the optical fiber.

5. The instrument of claim 4, further comprising means for delivering a biologically compatible flushing solution to an area surrounding the distal end of the pH probes.

6. The instrument of claim 4, further comprising means for controlling the depth of an incision created by operation of the sharp.

7. The instrument of claim 4, further comprising:

(a) electrical monitoring equipment in electrical communication with the electrically conductive needle for measuring and displaying fetal heart rate; and (b) illumination equipment in light transmitting communication with the fiber optic pH probes, which comprises at least:

(1) a light source in light transmitting communication with the optical fiber of each pH probe for transmitting light through the optical fiber into contact with the pH sensitive dye indicator composition;

(2) a light sensor in light transmitting communication with the optical fiber of each pH probe for sensing and displaying the pH indicative amount of fluorescent light generated by the pH sensitive dye indicator composition after the transmitted light contacts the dye.

8. The instrument of claim 7 wherein at least three pH probes are equidistantly spaced and encircle the electrically conductive needle.

9. The instrument of claim 1, further comprising means for delivering a biologically compatible flushing solution to a sampling area surrounding a distal end of the pH probes.

10. The instrument of claim 1, further comprising means for controlling the depth of an incision created by operation of the sharp.

11. The instrument of claim 1 wherein the pH probes are electrode cells, each of which include at least:

(a) a measuring electrode; and (b) a reference electrode.

12. The instrument of claim 11, further comprising:

(a) electrical monitoring equipment in electrical communication with the electrically conductive needle for measuring and displaying fetal heart rate; and (b) electrical monitoring equipment in electrical communication with each electrode cell for measuring and displaying the pH indicative electrical potential sensed by the electrodes.

13. The instrument of claim 1 comprising at least three pH probes.

* * * * *